United States Patent
Agrawal et al.

(10) Patent No.: US 11,434,184 B2
(45) Date of Patent: Sep. 6, 2022

(54) PROCESS TO PRODUCE ALKENES FROM SHALE GAS

(71) Applicant: PURDUE RESEARCH FOUNDATION, West Lafayette, IN (US)

(72) Inventors: Rakesh Agrawal, West Lafayette, IN (US); Zewei Chen, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 17/352,601

(22) Filed: Jun. 21, 2021

(65) Prior Publication Data

US 2021/0395169 A1  Dec. 23, 2021

Related U.S. Application Data

(60) Provisional application No. 63/042,377, filed on Jun. 22, 2020.

(51) Int. Cl.
*C07C 5/327*  (2006.01)
*C07C 7/04*  (2006.01)

(52) U.S. Cl.
CPC ............... *C07C 5/327* (2013.01); *C07C 7/04* (2013.01)

(58) Field of Classification Search
CPC .................. C07C 5/327; C07C 7/04
See application file for complete search history.

(56) References Cited

U.S. PATENT DOCUMENTS 10,662,132 B2 * 5/2020 Jo .......................... C07C 5/333

* cited by examiner

*Primary Examiner* — Thuan D Dang
(74) *Attorney, Agent, or Firm* — Edmonds & Cmaidalka, P.C.

(57) ABSTRACT

Systems and processes for producing one or more alkenes from shale gas. The process includes at least two dehydrogenation reactors whereby propane, or a mixture of propane and butane, can be dehydrogenated in a first reactor and ethane can be dehydrogenated in a second reactor. The lighter components which serve as chemical inert and thermal mass are separated from the dehydrogenated product after each reactor.

25 Claims, 5 Drawing Sheets

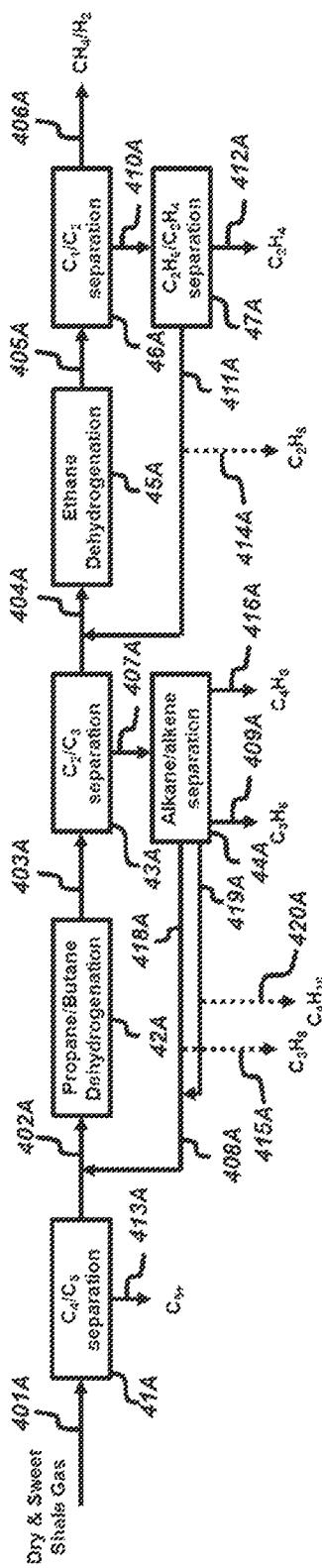
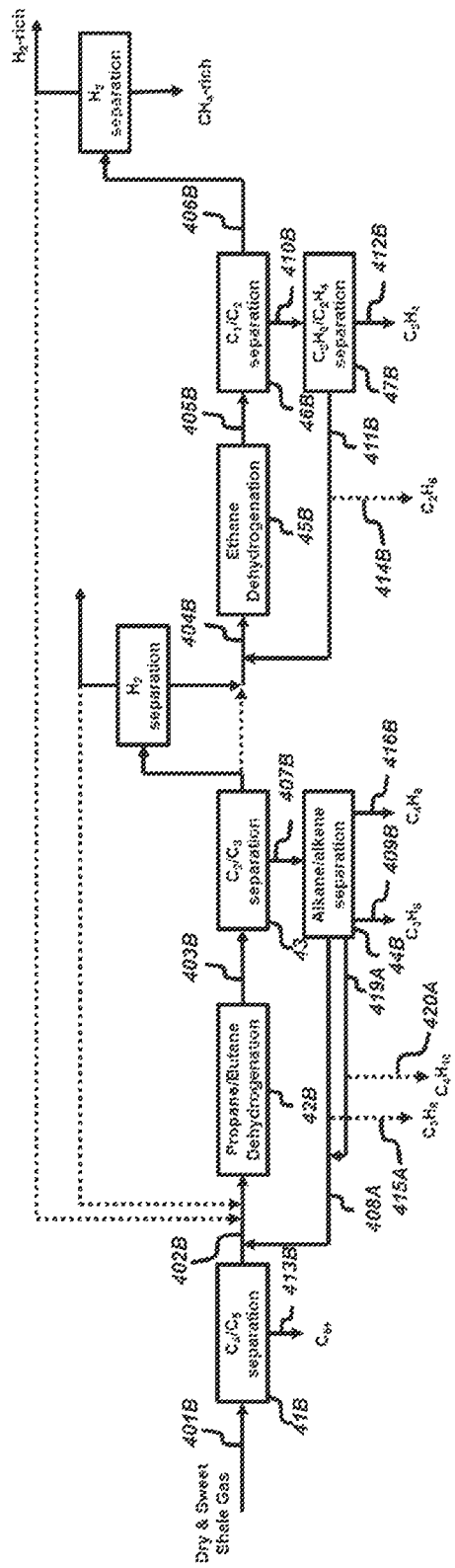
Figure 4A
Figure 4B

PROCESS TO PRODUCE ALKENES FROM SHALE GAS

CROSS-REFERENCE TO RELATED APPLICATIONS

This application claims priority to U.S. Provisional Patent Application having Ser. No. 63/042,377, filed on Jun. 22, 2020. The entirety of which is incorporated by reference herein.

GOVERNMENT LICENSE RIGHTS

This invention was made with government support under Cooperative Agreement No. EEC-1647722 awarded by the National Science Foundation. The government has certain rights in the invention.

BACKGROUND OF THE INVENTION

Field of the Invention

Embodiments provided herein relate to systems and processes for olefin production, including ethylene and propylene production from natural gas liquids in shale gas.

Description of the Related Art

Shale gas has become an increasingly important source of natural gas in the United States and it will become even more important in the future. The U.S. government's Energy Information Administration estimates that in 2017 about 62% of the total U.S. dry natural gas production comes from shale gas and by 2050, nearly 90% of the United States' natural gas production will come from shale resources. Shale gases contain substantial concentrations of natural gas liquids (NGLs), which are typically separated from methane at a natural gas processing plant. NGLs typically consist of C2H6, C3H8, C4H10 and C5H12.

Table 1 below provides a typical shale gas composition from wells at Barnett, Eagle Ford, and Bakken fields. It is worth noting that $CH_4$ is the predominant component of a shale gas stream (i.e. greater than 50 mol %). The combined mole fraction of all NGL components, $C_2$, $C_3$, $C_4$ and $C_{5+}$ alkanes, in a typical shale gas, generally varies from 5% to 40%.

TABLE 1

Shale Gas Compositions (in mol %) from Wells at Barnett, Eagle Ford, and Bakken fields.

|  | Barnett | Eagle Ford | Bakken |
|---|---|---|---|
| $CH_4$ | 85 | 74 | 58 |
| C2H6 | 6 | 14 | 20 |
| C3H8 | 2 | 5 | 11 |
| C4H10 | 2 | 3 | 4 |
| $C_{5+}$ | 0 | 2 | 1 |
| $N_2$ | 2 | 0 | 4 |
| $H_2O$ | 0.26 | 0.28 | 0.29 |
| $CO_2$ | 2 | 1 | 1 |
| $H_2S$ (mg/scf) | 335 | 307 | 115 |

FIG. 1 depicts a block flow diagram illustrating a prior art process for a conventional processing procedure of shale gas wherein acid gas such as $H_2S$ and $CO_2$, as well as water are removed from the raw shale gas to get dry and sweet shale gas, and then methane ($CH_4$) is removed from the sweet and dry shale gas and the remaining NGLs are further fractionated into pure ethane, pure propane, pure butane and $C_{5+}$ products. As shown in FIG. 1, the raw shale gas stream 101 first goes through an acid gas removal unit 10 to remove acid gas such as $H_2S$ and $CO_2$, followed by a dehydration unit 11 to remove water. The outlet stream 103 from the dehydration unit 11 is a dry and sweet shale gas stream, which then goes through an NGL recovery unit 12 where natural gas liquids 105 and $CH_4$-rich gas 104 are separated. Generally, a demethanizer distillation column is used for the separation of methane. The natural gas liquids stream 105 is further fractionated into a pure ethane stream 106, a pure propane stream 107, a pure butane stream 108, and a $C_{5+}$ condensate stream 109. Generally, natural gas liquids stream 105 is sent to a deethanizer column to recover ethane stream 106 and the bottom stream from this column is sent to a depropanizer column to distill propane in stream 107. The bottom from the depropanizer is sent to a debutanizer column to recover distillate butane stream 108. The bottoms from this column provides $C_{5+}$ condensate stream 109. The demethanizer, deethanizer, and depropanizer columns operate at subambient temperatures and are energy intensive. The $CH_4$-rich stream 104 could be directly sent to natural gas pipelines or other downstream processes. The recovered ethane and propane are primary feedstocks for ethylene and propylene production. The $C_{5+}$ condensate is often used to dilute highly viscous heavier oils.

Conventional technologies to produce olefins from shale gas resources are primarily steam cracking and catalytic dehydrogenation. While ethylene is primarily produced through steam cracking, on purpose propylene production is often through catalytic dehydrogenation, such as OLEFLEX™ from UOP and CATOFIN™ from Lummus Technology. Both steam cracking and catalytic dehydrogenation are capital and energy intensive. In the steam cracking process, process requirements such as water conditioning for steam generation, water boiling, stream superheating, and high pressure steam superheating prior to its introduction in the feed as well as steam condensation cum separation subsequent to the cracking reaction contribute very significantly to the process complexities and the costs associated with the process. Furthermore, use of streams at high temperatures adds to the cost as high-performance metal alloys are needed to withstand corrosive byproducts that are promoted by steam. In the catalytic dehydrogenation process, which is an endothermic reaction, the process feed and multiple adiabatic reaction beds in tandem are preheated to the reaction temperature to sustain the temperature needed. Moreover, the catalyst needs to be regenerated regularly since severe coking on the catalyst surface deteriorate the catalyst. Heat management around multiple reaction beds, catalyst regeneration and product purification are the major obstacles for a simple yet efficient process.

US patent application having application Ser. No. 16/832,092 discloses an alternative process for converting natural gas liquids to alkenes in the absence of steam. Referring to FIG. 2, a mixture of methane and other heavier paraffins 201 is directly sent to a cracker 20 where paraffins are cracked. Methane replaces steam as a diluent to lower the paraffin feed partial pressure. However, in this cracker, since a high temperature in the range of 700° C.-900° C. is used to dehydrogenate ethane, other alkane components heavier than ethane such as propane and butane are cracked into ethylene and methane, hence ethylene is the predominant product of this process while the production of heavier alkenes are very small.

WO2013/089859A1, discloses a process whereby diluent methane, nitrogen or argon is added to a pure light paraffin such as propane, or butane or pentane in a molar ratio of diluent to hydrocarbon in a range of 0.1:1 to 3.0:1. The mixture is then sent to a catalytic dehydrogenation unit of an Olefex™ process. To decrease the quantity of fresh methane addition to the pure propane, or butane or pentane feed, a methane separation is performed downstream of the dehydrogenation unit and is recycled to the hydrocarbon feed. Thus, a purified propane fraction obtained from a propylene recovery unit is mixed with a fresh methane feed and a methane-containing recycle stream and sent to a catalytic dehydrogenation reactor at a temperature in the range of 550 to 700° C. The dehydrogenation reactor outlet stream, in addition to propylene, also contains light hydrocarbon byproducts from the cracking of propane such as methane, ethane, ethylene etc. These light hydrocarbon byproducts along with hydrogen from the dehydrogenation are then separated from propylene and unconverted propane. This again requires energy intensive separations, especially for methane, ethane and other hydrocarbon components lighter than propane. A similar separation is performed to provide pure propane to the dehydrogenation unit. The recycle methane is also separated from the ethane and other molecules containing two carbon atoms in the reactor product stream to avoid buildup of such molecules in the recycle stream. Due to this duplication of separation steps, not only more energy is consumed but more equipment is employed contributing to increased capital expenditure. When pure butane from the fractionation unit 15 is used to produce butylenes per the teaching of WO2013/089859A1, the deficiencies discussed in the context of propane are repeated, leading to further duplication and process complexity.

There is still a need, therefore, for a simpler and more efficient process for producing olefins, such as butylenes, propylene, ethylene etc. from shale gas.

SUMMARY OF THE INVENTION

Systems and processes for more efficiently upgrading natural gas liquids are provided. In one embodiment, a process for producing alkenes from shale gas comprises two dehydrogenation reactors wherein propane (or a mixture of propane and butane) is dehydrogenated in a first reactor and ethane is dehydrogenated in a second reactor. The lighter components which serve as chemical inert and thermal mass are separated from the dehydrogenated product after each reactor.

In certain embodiments, the effluent stream from the first dehydrogenation reactor can be separated to provide a stream comprising methane and C2 hydrocarbons, which can be fed to the second dehydrogenation reactor.

The embodiments provided herein are beneficial for the production of useful butylenes, propylene and ethylene product streams from shale gas or any natural gas stream containing methane, ethane, propane and butane.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments. It is emphasized that the figures are not necessarily to scale and certain features and certain views of the figures can be shown exaggerated in scale or in schematic for clarity and/or conciseness.

FIG. 4A is a block diagram of another illustrative process for producing alkenes from a hydrocarbon feed stream, according to one or more embodiments described herein. The process includes two dehydrogenation reactors whereby propane and butane are both dehydrogenated in the first reactor and ethane is dehydrogenated in the second reactor. The lighter components which serve as chemical inert and thermal mass are separated from the dehydrogenated products after each reactor.

FIG. 4B is a block diagram of another illustrative process for producing alkenes from a hydrocarbon feed stream, according to one or more embodiments described herein. The process includes two dehydrogenation reactors whereby propane and butane are both dehydrogenated in the first reactor and ethane is dehydrogenated in the second reactor. The lighter components which serve as chemical inert and thermal mass are separated from the dehydrogenated products after each reactor. A portion of the hydrogen is separated after at least one of the reactors and a portion of produced hydrogen is fed back to the propane/butane dehydrogenation reactor.

DETAILED DESCRIPTION

Figure 1:
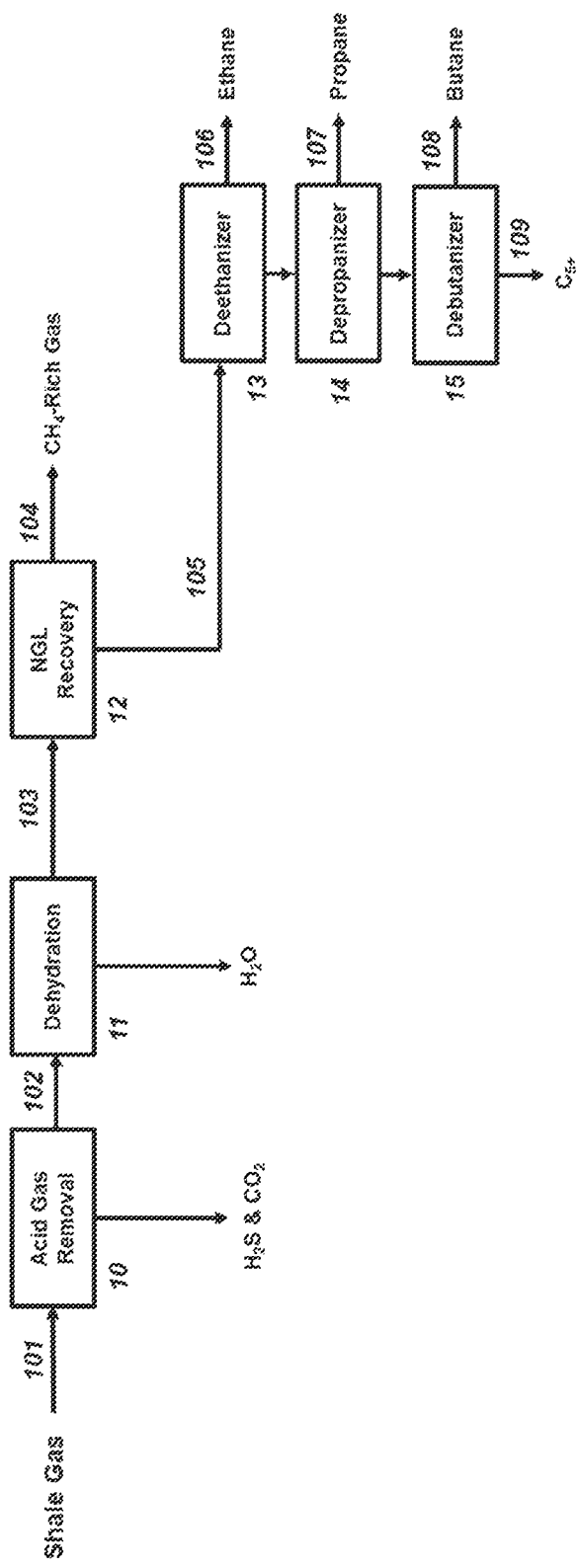
FIG. 1 depicts a block flow diagram illustrating a prior art process for a conventional processing procedure of shale gas wherein acid gas such as $H_2S$ and $CO_2$, as well as water are removed from the raw shale gas to get dry and sweet shale gas, and then methane ($CH_4$) is removed from a sweet and dry shale gas and the remaining NGLs are further fractionated into pure ethane, pure propane, pure butane and $C_{5+}$ products.
Figure 2:
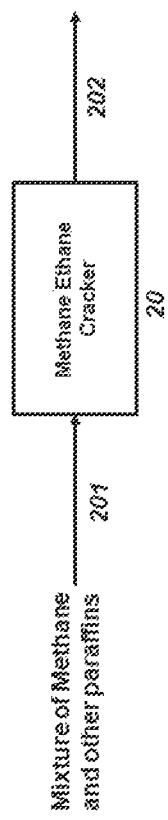
FIG. 2 is a block diagram illustrating a thermal cracking process whereby paraffins in shale gas are converted to olefins in the absence of steam and without frontend separations.

A detailed description will now be provided. It is to be understood that the following disclosure describes several exemplary embodiments for implementing different features, structures, or functions of the invention. Exemplary embodiments of components, arrangements, and configurations are described below to simplify the present disclosure; however, these exemplary embodiments are provided merely as examples and are not intended to limit the scope of the invention. Additionally, the present disclosure can repeat reference numerals and/or letters in the various exemplary embodiments and across the Figures provided herein. This repetition is for the purpose of simplicity and clarity and does not in itself dictate a relationship between the various exemplary embodiments and/or configurations discussed in the Figures. The exemplary embodiments presented below also can be combined in any combination of ways, i.e., any element from one exemplary embodiment can be used in any other exemplary embodiment, without departing from the scope of the disclosure.

Additionally, certain terms are used throughout the following description and claims to refer to particular components. As one skilled in the art will appreciate, various entities can refer to the same component by different names, and as such, the naming convention for the elements described herein is not intended to limit the scope of the invention, unless otherwise specifically defined herein. Further, the naming convention used herein is not intended to distinguish between components that differ in name but not function.

The terms "including" and "comprising" are used in an open-ended fashion, and thus should be interpreted to mean "including, but not limited to." The phrase "consisting essentially of" means that the described/claimed composition does not include any other components that will materially alter its properties by any more than 5% of that property, and in any case, does not include any other component to a level greater than 3 wt %.

The indefinite articles "a" and "an" refer to both singular forms (i.e., "one") and plural referents (i.e., one or more) unless the context clearly dictates otherwise.

The term "or" is intended to encompass both exclusive and inclusive cases, i.e., "A or B" is intended to be synonymous with "at least one of A and B," unless otherwise expressly specified herein.

The terms "up" and "down"; "upward" and "downward"; "upper" and "lower"; "upwardly" and "downwardly"; "above" and "below"; and other like terms as used herein refer to relative positions to one another and are not intended to denote a particular spatial orientation since the apparatus and methods of using the same can be equally effective at various angles or orientations.

The term "alkane" and "paraffin" are used interchangeably, and both refer to saturated compounds containing hydrogen and carbon only, in which all the carbon-carbon bonds are single. The term alkane encompasses linear, branched, and saturated cyclic alkanes.

The terms "alkene" and "olefin" are used interchangeably, and both refer to any unsaturated hydrocarbon containing one or more pairs of carbon atoms linked by a double bond. Such unsaturated hydrocarbons include cyclic or aliphatic olefins, and include mono-olefins, di-olefins, tri-olefins, etc.

The terms "hydrocarbon feed stream" and "hydrocarbon feed mixture" are used interchangeably and both refer to any stream of hydrocarbons that are derived directly from a zone or formation within the earth. Illustrative streams can be or can include a raw shale gas stream or raw natural gas stream or other raw hydrocarbon gaseous stream that is obtained directly (i.e. without processing to remove water and/or acid gas) from a reservoir, wellhead, or pipeline. Illustrative streams can also be or can also include a natural gas stream that is obtained by passing raw natural gas pipelined from a reservoir or wellhead through one or more acid gas removal and dehydration units (i.e. after processing to remove water and/or acid gas). Suitable streams can also originate from a refinery, such as from a FCC, coker, steam cracker, and pyrolysis gasoline (pygas). Suitable streams can also be or can include shale gas, syngas and/or coal gas. For simplicity and ease of description, the detailed description provided herein refers to "shale gas" or "natural gas" or "sweet and dry shale gas" although the embodiments of the present invention equally apply to any hydrocarbon containing at least 5 mol % NGL, regardless of how or where the hydrocarbon is obtained.

The term "cracking" refers to a process in which saturated hydrocarbons are broken down into smaller, often unsaturated, hydrocarbons. It is the principal industrial method for producing lighter alkenes (or commonly olefins), including ethene (or ethylene) and propene (or propylene). Steam cracker units are facilities in which a feedstock such as naphtha, liquefied petroleum gas (LPG), ethane, propane or butane is thermally cracked with steam in one or more furnaces to produce lighter hydrocarbons.

The term "dehydrogenation" refers to a chemical reaction that involves the removal of hydrogen from an organic molecule.

The terms "downstream processes" and "downstream processing" are used interchangeably and refer to any one or more processing steps and/or unit operations for quenching, heating, cooling, separation, distillation, sequestration, and/or further reactions including polymerization, alkylation, and oligomerization.

The term "$C_n$" hydrocarbon wherein n is a positive integer, e.g., 1, 2, 3, 4, or 5, means hydrocarbon having n carbon atom(s) per molecule. The term "$C_{n+}$" hydrocarbon wherein n is a positive integer, e.g., 1, 2, 3, 4, or 5, means a hydrocarbon mixture containing Cn and higher hydrocarbons.

The term "$C_n/C_{n+1}$ separations" refers to any technology or device that separates one stream containing $C_n$ and $C_{n+1}$ to two streams wherein one stream contains $C_n$ but very little $C_{n+1}$ while another stream contains $C_{n+1}$ but very little $C_n$. When a mixture containing C and $C_{n+1}$ molecules also contains molecules with a number of carbon atoms less than $C_n$ such as $C_{n-1}$ and/or $C_{n-2}$ etc. and/or molecules with a number of carbon atoms more than $C_{n+1}$ such as $C_{n+2}$ and/or $C_{n+3}$, then $C_n/C_{n+1}$ separations refers to a first stream containing $C_n$ and any smaller molecules ($C_{n-1}$ etc.) and a second stream containing $C_{n+1}$ and any larger molecules ($C_{n+2}$ etc.).

The term "shale gas" refers to natural gas that is produced from a shale or other tight formation, is a gaseous phase mixture containing natural gas liquids, acid gases, water, nitrogen ($N_2$), and possibly trace amounts of contaminants. A suitable shale gas (or natural gas) contains at least 30 mol % $CH_4$ and preferably at least 50 mol % $CH_4$ and up to 50 mol % of $C_2H_6$, $C_3H_8$, $C_4H_{10}$, and/or $C_{5+}$ hydrocarbons. For example, a suitable shale gas (or natural gas) contains about 60 mol % to about 95 mol % $CH_4$ and about 5 mol % to about 40 mol % of $C_2H_6$, $C_3H_8$, $C_4H_{10}$, and/or $C_{5+}$ hydrocarbons (or collectively referred to as "$C_{2+}$ hydrocarbons" or "$C_{2+}$ alkanes"). Among the $C_{2+}$ hydrocarbons, $C_2H_6$ is generally the highest concentration followed by $C_3H_8$ then $C_4H_{10}$. Nitrogen gas ($N_2$) can also be present in the shale gas. When $N_2$ is present in the shale gas, it can be left with methane to travel through the dehydrogenation reactors.

The term "raw shale gas" refers to shale gas that is pipelined from reservoirs or wellheads prior to any further processing.

The term "sweet and dry shale gas" refers to shale gas obtained after acid gases and water have been removed from the raw shale gas. Insignificant amounts of other components in the sweet shale gas can be removed together with water and thus, a sweet and dry shale gas has almost all the components contained in raw shale gas except acid gases and water. Since acid gases and water can be in relatively small concentration, the composition of the sweet and dry shale gas is similar, or substantially the same, as that of the raw shale gas.

The term "sweet shale gas" refers to shale gas obtained after the acid gases have been removed from the raw shale gas. Insignificant amounts of other components in the raw shale gas can be removed together with acid gases and thus, a sweet shale gas has almost all the components contained in raw shale gas except acid gases.

The term "steam methane reforming" or "SMR" refers to a method for producing syngas (hydrogen and carbon monoxide) by reaction of hydrocarbons with water. Commonly natural gas is the feedstock. The main purpose of this technology is hydrogen production.

Each of the appended claims defines a separate invention, which for infringement purposes is recognized as including equivalents to the various elements or limitations specified in the claims. Depending on the context, all references to the "invention" may in some cases refer to certain specific embodiments only. In other cases, it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions, when the information in this disclosure is combined with publicly available information and technology.

The following detailed description illustrates embodiments of the present disclosure. These embodiments are described in enough detail to enable a person of ordinary skill in the art to practice these embodiments. It should be understood, however, that the embodiments and examples described herein are given by way of illustration only, and not by way of limitation, the embodiments are chosen and described so that others skilled in the art may appreciate and understand the principles and practices of the present teachings. Various substitutions, modifications, additions, and rearrangements can be made that remain potential applications of the disclosed processes. Therefore, the description that follows is not to be taken as limiting on the scope of the appended claims. In particular, an element associated with a particular embodiment should not be limited to association with that particular embodiment but should be assumed to be capable of association with any embodiment discussed herein.

Figure 3A:
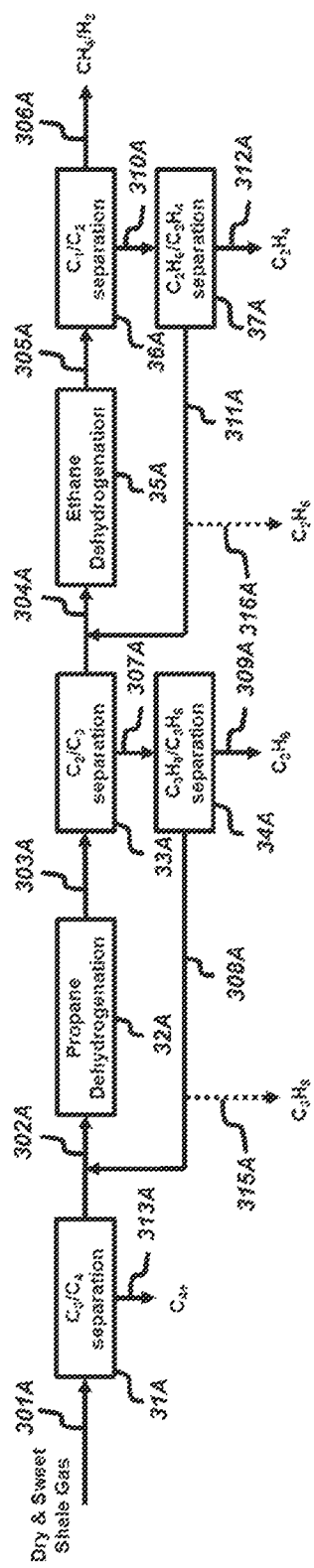
FIG. 3A is a block diagram of an illustrative process for producing alkenes from a hydrocarbon feed stream, according to one or more embodiments described herein. The process includes two dehydrogenation reactors whereby propane is dehydrogenated in a first reactor and ethane is dehydrogenated in a second reactor. The lighter components which serve as chemical inert and thermal mass are separated from the dehydrogenated product after each reactor.

FIG. 3A is a block diagram of an illustrative process for producing alkenes from a hydrocarbon feed stream, according to one or more embodiments. A dry and sweet shale gas stream 301A can be obtained by passing the raw shale gas through acid gas removal and dehydration, and can be fed to a $C_3/C_4$ separation unit 31A. In this unit, $C_4$ and the molecules heavier than $C_4$ can be separated from $C_3$ and molecules lighter than $C_3$. The stream 302A which contains $C_3$ and components lighter than $C_3$ can be fed to a propane dehydrogenation reactor 32A, the propane dehydrogenation reactor can be operated at a temperature around 500~700° C., preferably 600~675° C., and a pressure 1~30 bar.

A catalyst can be used to accelerate the reaction rate and increase the selectivity towards propylene. Any suitable dehydrogenation catalyst can be used. One example is described in U.S. Pat. No. 6,756,340. It is worth noticing that in the reactor, all the hydrocarbons lighter than propane such as methane and ethane serve as a chemical inert and provide thermal mass. When nitrogen is present in the feed, it also acts as inert and provides thermal mass. The existence of those lighter hydrocarbons in the dehydrogenation reactor (i.e. the inert and thermal mass) decreases the partial pressure of propane which results in a higher conversion of propane to propylene. Moreover, the dehydrogenation reaction is an endothermic reaction, which requires heat supply to the reactor. The commercial catalytic dehydrogenation process, for instance, OLEFLEX™ from UOP, requires multiple preheated reaction beds. In other words, the reaction beds serve as thermal mass to maintain the temperature of the reaction. Despite this, significant temperature drop is observed for the stream out of those reaction beds and hence intermediate heating steps are needed. This sophisticated design poses a challenge for building and controlling the process. In the current process, the lighter hydrocarbons including methane and ethane serve as thermal mass to mitigate the temperature drop in the reaction beds. Therefore, the number of reaction beds decreases, which significantly improves the economics of this process.

The stream 303A out of the propane dehydrogenation reactor 32A can contain propane, propylene, ethane, a little ethylene, methane, and hydrogen and any other light inert component if present in stream 301A. Stream 303A can be sent to a $C_2/C_3$ separation unit 33A where $C_3$ can be separated in stream 307A from hydrocarbons lighter than $C_3$ in stream 304A. This $C_2/C_3$ separation unit 33A can be any separation unit including, but not limited to distillation, absorption, membrane, membrane cascade, condensation, adsorption and any combination thereof. The hydrocarbons in stream 307A can be further separated in a $C_3H_8/C_3H_6$ separation unit 34A wherein propane and propylene are separated from each other in stream 308A and 309A respectively. Again, this $C_3H_8/C_3H_6$ separation unit 34A can be any separation unit including, but not limited to distillation, absorption, membrane, membrane cascade, condensation, adsorption and any combination thereof. Propane in stream 308A can be recycled back to the propane dehydrogenation unit 32A, and propylene in stream 309A can be collected as the product. If needed, a portion or all of stream 308A could be collected as propane product stream 315A. Stream 304A out of the $C_2/C_3$ separation unit 33A could be sent to an ethane dehydrogenation unit 35A wherein ethane is dehydrogenated into ethylene and hydrogen. This ethane dehydrogenation unit can be a thermal dehydrogenation unit operated at 700~950° C., preferably 800~900° C. and 1~30 bar. The ethane dehydrogenation unit may or may not use catalyst. The heat supplied to the reactor could either come from a furnace or from an electrically heated device.

The stream 305A out of the ethane dehydrogenation reactor 35A includes ethane, ethylene, methane, and hydrogen. It can be sent to a $C_1/C_2$ separation unit 36A wherein $C_2$ hydrocarbons can be separated in stream 310A from $C_1$ and hydrogen in stream 306A. If any light inerts such as nitrogen are present in stream 301A, they will also be found in stream 306A. $C_2$ containing stream 310A can be further separated into ethane-rich stream 311A and ethylene product stream 312A in an ethane/ethylene separation unit 37A wherein ethane and ethylene are separated. Again, these two separation units could be any separation unit including, but not limited to distillation, absorption, membrane, membrane cascade, condensation, adsorption, and any combination thereof. Ethane can be recycled to the ethane dehydrogenation unit 35A, and ethylene in stream 312A can be collected as the product. If needed, a portion or all recycle ethane rich stream 311A can be collected as ethane product stream in line 316A.

A number of catalytic dehydrogenation processes for propane and butane use catalysts that requires introduction of hydrogen in the feed to the reactor. For example, Oleflex™ process recommends hydrogen to propane or butane molar ratio in the range of 0.1:1 to 1.0:1 with the preferred ratio around 0.6 to 0.8. For such catalytic dehydrogenation processes, the process in FIG. 3B allows two possible locations from where hydrogen can be separated and recycled to the dehydrogenation unit 32B. In one embodiment, a hydrogen rich stream can be recovered from $CH_4$ and $H_2$ stream 306B and recycled to the inlet of the dehydrogenation unit 32B to provide the needed molar ratio of hydrogen to propane. An alternative is to send a portion or all of stream 317B to a hydrogen separation unit and a $H_2$-rich stream is recycled to the stream 302B prior to its entry in the catalyst bed. Any suitable process to recover hydrogen-rich stream may be employed including absorption, adsorption, membrane etc. Since the concentration of hydrogen would be highest in the methane-rich stream 306B from the $C_1/C_2$ separation unit 310B, it will be a preferred stream to recover hydrogen. A hydrogen selective membrane unit may be used for this purpose.

The propane catalytic dehydrogenation unit can be operated at pressures ranging from close to 1 bar absolute up to 30 bar absolute. Generally the preferred operating pressure range taught in the literature is from 1 bar absolute to 3.5 bar absolute. However, as observed from Table 1, due to the presence of methane and ethane into shale gas, the partial pressure of propane is around one-tenth or lower than the total pressure of the stream. Thus one of the advantages of the embodiments provided herein is that the catalytic dehydrogenation reactor can be operated at a much higher total pressure while providing high conversions. Furthermore, a lower mole fraction of propane in the feed, compared to cases where propane concentration in the feed is 35%~62% range, implies that the rest of the components will provide more thermal energy for propane dehydrogenation and for the same temperature drop across the reactor, an increased propane dehydrogenation will be achieved.

The product streams can be sent to one or more downstream processes. All the alkene products, for example, could be directly sold as final products, or go through oligomerization processes to produce liquid hydrocarbons, or go through polymerization processes to produce polymers, or go through an alkylation process to produce alkylated molecules, or go through any other possible downstream processes. The methane stream could also be directly sent to pipelines as commercial natural gas, or go through steam methane reforming to product syngas, or go through any other possible downstream processes.

Figure 3B:
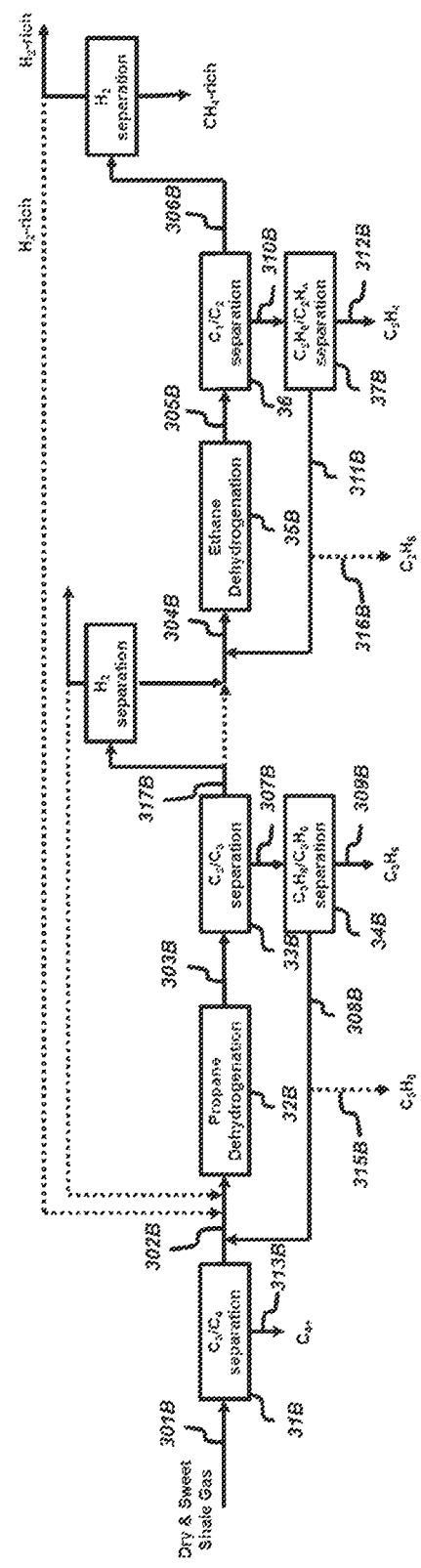
FIG. 3B is a block diagram of another illustrative process for producing alkenes from a hydrocarbon feed stream, according to one or more embodiments described herein. The process includes two dehydrogenation reactors whereby propane is dehydrogenated in a first reactor and ethane is dehydrogenated in a second reactor. A portion of the hydrogen is separated after at least one of the reactors and a portion of produced hydrogen is fed back to the propane dehydrogenation reactor.

FIGS. 4A and 4B depicts alternative flow diagrams for producing alkenes from a hydrocarbon feed stream, according to one or more embodiments described herein. The difference between the configurations in FIG. 3A and the configuration in FIG. 4A is that, in FIG. 4A, the feed gas in stream 401A first goes through a $C_4/C_5$ separation unit, then butane and propane in stream 402A are dehydrogenated into butylene and propylene in the same dehydrogenation unit 42A. While in FIG. 3A, the butane in stream 301A is separated in the $C_3/C_4$ separation unit 31A without going into any dehydrogenation reactor. The stream 403A out of the propane/butane dehydrogenation unit 42A is separated in to two streams: stream 404A containing $C_2$ and components lighter than $C_2$ and stream 407A contains $C_3$ and components heavier $C_3$. Stream 404A is fed to an ethane dehydrogenation 45A and other downstream processes. These downstream processes are identical for both configurations in FIG. 3A and FIG. 4A. Stream 407A goes to a $C_3/C_4$ as well as an alkane/alkene separation unit 44A in which $C_3$, $C_4$ alkanes and $C_3$, $C_4$ alkenes are separated. The $C_3$ alkane in stream 418A as well as $C_4$ alkanes in stream 419A are mixed in stream 408A and send back to the propane/butane dehydrogenation unit 42 and $C_3$, $C_4$ alkenes in stream 409A and 416A are collected as products. It is worth noticing that alkane/alkene separation unit 44A may not be a single equipment, or a single-step process. For example, it could be a separation system such as distillation trains separates stream 407A into butane, butylene, propane, and propylene four products. The advantage of this configuration is the production of butylene. This is especially beneficial when the feed contains significant amount of butane. However, the propane/butane dehydrogenation reactor requires a catalyst to handle both propane and butane. Similar to the case for propane dehydrogenation in FIG. 3B, hydrogen can be recycled to the propane/butane dehydrogenation reactor in FIG. 4B. The benefits due to the presence of methane, ethane and possibly some nitrogen from feed stream 401B for the dehydrogenation reactor describe in the context of FIG. 3B will also be applicable here. In FIG. 3B, the $H_2$ to $C_3$ ratio is from 0.1:1 to 1:1, while in FIG. 4B, the $H_2$ to $(C_3+C_4)$ ratio is 0.1:1 to 1:1.

For some shale gases, such as the Barnett in Table 1, concentration of methane approaches to relatively high values of 85% and propane concentration to a low value of 2%. While this shale gas stream is still suitable for propane and ethane dehydrogenation as disclosed in the current invention, under certain circumstances, it may be desirable to reduce methane concentration to decrease the equipment size of all the processing units in either FIG. 3 or 4. Under such scenario, dry and sweet shale gas stream can be send to a separation unit to remove a fraction of the methane. Thus Barnett shale gas, after acid gas removal and drying, is fed to a separation unit to remove 20 mole % to 75 mol % of methane contained in the feed. The remaining stream will contain 80 mole % to 25 mol % of methane from the original gas stream as well as all other $C_{2+}$ hydrocarbons. This stream is then sent for dehydrogenation of butane, propane, and ethane. The separation of methane from the sweet and dry shale gas can be performed by any suitable separation process including condensation, distillation, adsorption, absorption and, membrane or combination thereof.

Figure 5A:
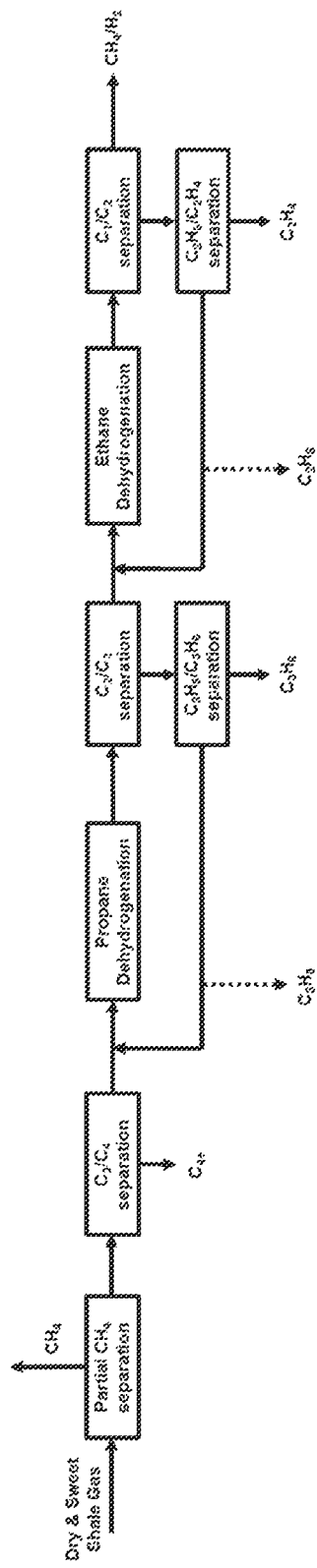
FIG. 5A is a block diagram of another illustrative process for producing alkenes from a hydrocarbon feed stream, according to one or more embodiments described herein. The process includes two dehydrogenation reactors whereby propane is dehydrogenated in the first reactor and ethane is dehydrogenated in the second reactor. A portion of methane is separated before the rest of the feed is sent to the dehydrogenation reactors. The lighter components which serve as chemical inert and thermal mass are separated from the dehydrogenated product after each reactor.

The related processes are depicted in FIGS. 5A, 5B, 6A, and 6B. FIG. 5A is a block diagram of another illustrative process for producing alkenes from shale gas, according to one or more embodiments described herein. The process includes two dehydrogenation reactors whereby propane is dehydrogenated in the first reactor and ethane is dehydrogenated in the second reactor. A portion of methane is separated before the rest of the feed is sent to the dehydrogenation reactors. The lighter components which serve as chemical inert and thermal mass are separated from the dehydrogenated product after each reactor.

Figure 5B:
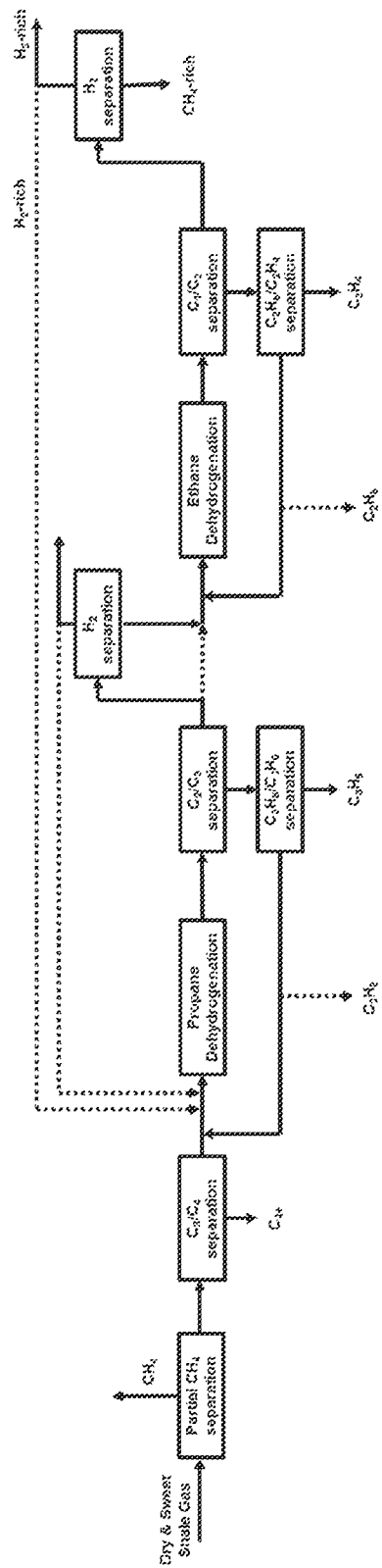
FIG. 5B is a block diagram of another illustrative process for producing alkenes from a hydrocarbon feed stream, according to one or more embodiments described herein. The process includes two dehydrogenation reactors whereby propane is dehydrogenated in the first reactor and ethane is dehydrogenated in the second reactor. A portion of methane is separated before the rest of the feed is sent to the dehydrogenation reactors. The lighter components which serve as chemical inert and thermal mass are separated from the dehydrogenated product after each reactor. A portion of the hydrogen is separated after at least one of the reactors and a portion of produced hydrogen is fed back to the propane dehydrogenation reactor.

FIG. 5B is a block diagram of another illustrative process for producing alkenes from a hydrocarbon feed stream, according to one or more embodiments described herein. The process includes two dehydrogenation reactors whereby propane is dehydrogenated in the first reactor and ethane is dehydrogenated in the second reactor. A portion of methane is separated before the rest of the feed is sent to the dehydrogenation reactors. The lighter components which serve as chemical inert and thermal mass are separated from the dehydrogenated product after each reactor. A portion of the hydrogen is separated after at least one of the reactors and a portion of produced hydrogen is fed back to the propane dehydrogenation reactor.

Figure 6A:
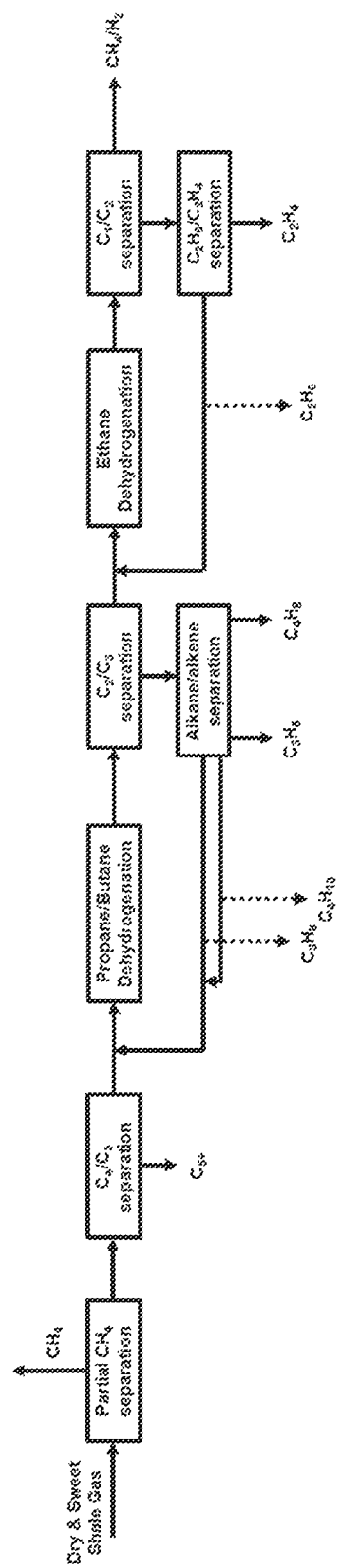
FIG. 6A is a block diagram of another illustrative process for producing alkenes from a hydrocarbon feed stream, according to one or more embodiments described herein. The process includes two dehydrogenation reactors whereby propane and butane are both dehydrogenated in the first reactor and ethane is dehydrogenated in the second reactor. A portion of methane is separated before the rest of the feed is sent to the dehydrogenation reactors. The lighter components which serve as chemical inert and thermal mass are separated from the dehydrogenated products after each reactor.

FIG. 6A is a block diagram of another illustrative process for producing alkenes from a hydrocarbon feed stream, according to one or more embodiments described herein. The process includes two dehydrogenation reactors whereby propane and butane are both dehydrogenated in the first reactor and ethane is dehydrogenated in the second reactor. A portion of methane is separated before the rest of the feed is sent to the dehydrogenation reactors. The lighter components which serve as chemical inert and thermal mass are separated from the dehydrogenated products after each reactor.

Figure 6B:
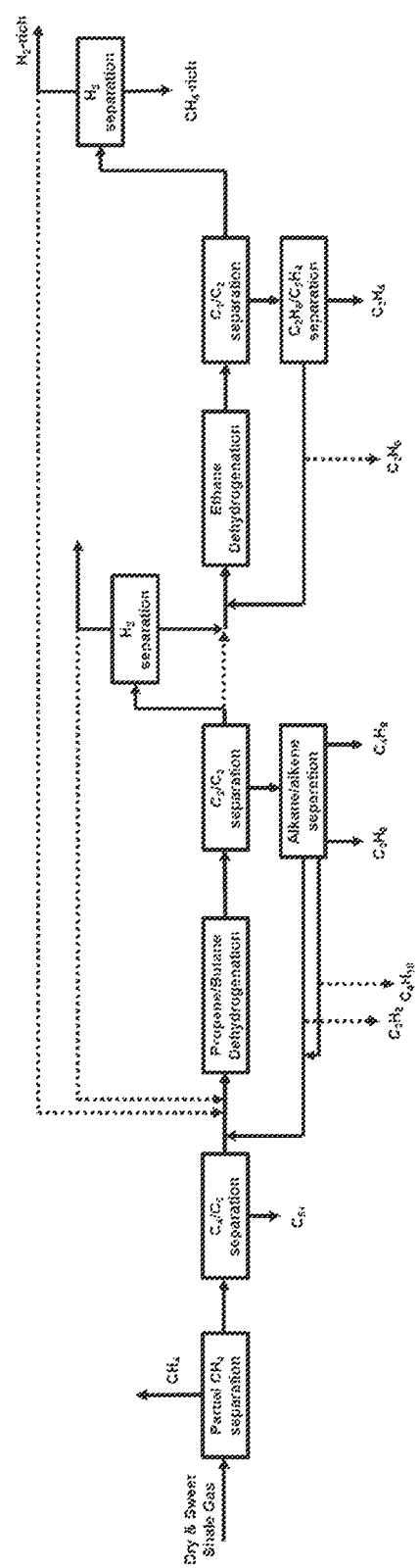
FIG. 6B is a block diagram of another illustrative process for producing alkenes from a hydrocarbon feed stream, according to one or more embodiments described herein. The process includes two dehydrogenation reactors whereby propane and butane are both dehydrogenated in the first reactor and ethane is dehydrogenated in the second reactor. A portion of methane is separated before the rest of the feed is sent to the dehydrogenation reactors. The lighter components which serve as chemical inert and thermal mass are separated from the dehydrogenated products after each reactor. A portion of hydrogen is separated after at least one of the reactors and a portion of produced hydrogen is fed back to the propane dehydrogenation reactor.

FIG. 6B is a block diagram of another illustrative process for producing alkenes from a hydrocarbon feed stream, according to one or more embodiments described herein. The process includes two dehydrogenation reactors whereby propane and butane are both dehydrogenated in the first reactor and ethane is dehydrogenated in the second reactor. A portion of methane is separated before the rest of the feed is sent to the dehydrogenation reactors. The lighter components which serve as chemical inert and thermal mass are separated from the dehydrogenated products after each reactor. A portion of hydrogen is separated after at least one of the reactors and a portion of produced hydrogen is fed back to the propane dehydrogenation reactor.

Prophetic Examples

The foregoing discussion can be further described with reference to the following non-limiting prophetic examples.

Process simulation results are provided for the processes described above with reference to FIGS. 3A and 3B. The process simulations were implemented by Aspen Plus. The feed information, including composition, flowrate, temperature, and pressure, is based on a typical shale gas stream from Bakken, which is shown in Table 1. All the separations are assumed to have complete separation. The conversion of the major reaction in all the dehydrogenation reactors of all three processes were set to be 90% of the equilibrium value. Besides major reactions, some key side reactions are also simulated. In the propane dehydrogenation reactors 32A and 32B, 20% of propane is assumed to be cracked into $C_2H_4$ and $CH_4$. In the ethane dehydrogenation reactor 35A and 35B, 10% of ethane is assumed to react with hydrogen and produce methane. A 0.21 bar pressure drop is assumed for all the unit operations in all the flowsheets. The stream information of the simulation is summarized in Table 2, Table 3, Table 4, and Table 5 provided below.

Table 2 summarizes the key stream information of a simulation for the process depicted in FIG. 3A where the two dehydrogenation reactors are operated at low pressures around 2~3 bar. As shown in Table 2, the yield of $C_3H_6$ in the propane dehydrogenation reactor is 62.3% per pass and the yield of $C_2H_6$ in the ethane dehydrogenation reactor is 71.6% per pass.

Table 3 summarizes the key stream information of a simulation for the process depicted in FIG. 3A where the two dehydrogenation reactors are operated at high pressures around 9~10 bar. As shown in Table 3, the yield of $C_3H_6$ in the propane dehydrogenation reactor is 41.5% per pass and the yield of $C_2H_6$ in the ethane dehydrogenation reactor is 49.2% per pass. The high pressure operation decreases $C_3H_6$ yield per pass in the propane dehydrogenation reactor and $C_2H_4$ yield per pass in the ethane dehydrogenation reactor. However, the reactor volume will be smaller. High pressure operation also potentially eliminates some equipment and makes the process simpler. For example, if the separation processes after those reactors are membrane separations, which need high pressure feeds to provide driving force across the membrane, then the high pressure reactors are particularly beneficial because they produce streams that are already pressurized.

Table 4 summarize the key stream information of a simulation for the process depicted in FIG. 3B with two $H_2$ separation units. In table 4, the yield of $C_3H_6$ in the propane dehydrogenation reactor is 54.2% per pass and the yield of $C_2H_6$ in the ethane dehydrogenation reactor is 78.3% per pass.

Table 5 summarize the key stream information of a simulation for the process in FIG. 3B with only one $H_2$ separation unit after $C_1/C_2$ separation. In table 4, the yield of $C_3H_6$ in the propane dehydrogenation reactor is 54.2% per pass and the yield of $C_2H_6$ in the ethane dehydrogenation reactor is 69.9% per pass.

By using methane as a diluent and performing propane (plus butane) along with ethane dehydrogenation in successive steps, the embodiments provided herein provide multiple advantages. For example, after propane dehydrogenation, only C3 components are separated and the separation of methane and hydrogen is delayed after the ethane dehydrogenation. As a result, methane beneficially acts as a diluent for the ethane dehydrogenation to ethylene by increasing conversion of ethane to ethylene. It avoids the inefficiencies and costs associated with the use of steam as a diluent in conventional steam ethane crackers to produce ethylene. Separation of any ethylene and methane byproducts formed in the propane dehydrogenation reactor are delayed after the ethane dehydrogenation reactor. Furthermore, presence of ethane in the propane dehydrogenation reactor lowers the partial pressure of propane leading to higher conversion of propane to propylene. These are synergistic effects which lead to process equipment simplification and improvement in process efficiency.

The beneficial impact of the current process is even greater in the context of shale gas or any natural gas stream containing methane, ethane, propane and butane. As shown in FIG. 1, the current practice teaches use of NGL recovery ($C_1/C_{2+}$ separation) followed by fractionation using $C_2/C_{3+}$, $C_3/C_{4+}$, and $C_4/C_{5+}$ separations to provide pure $C_2H_6$, $C_3H_8$, $C_4H_{10}$ and $C_{5+}$ streams. Then in order to benefit propane dehydrogenation, according to W2013/08985A1, fresh methane is added to $C_3H_8$ prior to dehydrogenation and subsequent to dehydrogenation a series of expanders and separation columns are used inside a cold box to separate methane in the feed and unwanted byproducts methane, $C_2$ hydrocarbons, hydrogen and propane from propylene. Thus separations such as $C_1/C_{2+}$ and $C_2/C_3$ which are performed in the first place on the shale gas to provide pure propane are employed again consuming energy and requiring another expansive cold box. When a process depicted in FIG. 3 is compared to that of a prior art process of FIG. 1, both processes use $C_2/C_3$, $C_3/C_4$, and $C_1/C_2$ separation units or similar separation units, and yet the process of FIG. 3 provides pure propylene and ethylene product streams. The embodiments described herein are beneficial for the production of useful butylenes, propylene and ethylene product streams from shale gas or a natural gas stream containing methane, ethane, propane and butane.

TABLE 2

Major Stream Information for the configuration in FIG. 3A wherein the two dehydrogenation reactors are at low pressures (2~3 bar)

|  | Sweet and dry shale gas 301A | Propane dehydrogenation inlet 302A | Propane dehydrogenation outlet 303A | Ethane dehydrogenation inlet 304A | Ethane dehydrogenation outlet 305A |
|---|---|---|---|---|---|
| Temperature (° C.) | 25 | 650 | 650 | 850 | 850 |
| Pressure (bar) | 30 | 2.58 | 2.37 | 2.16 | 1.95 |
| Flowrate (kmol/h) | 4749 | 4694 | 5395 | 4924 | 5677 |
| $N_2$ | 78 | 78 | 78 | 78 | 78 |
| $H_2$ | 0 | 0 | 611 | 611 | 1263 |
| $CH_4$ | 2866 | 2866 | 2956 | 2956 | 3156 |
| $C_2H_6$ | 991 | 991 | 853 | 1051 | 199 |
| $C_3H_8$ | 563 | 759 | 196 | 0 | 0 |
| $C_4H_{10}$ | 188 | 0 | 0 | 0 | 0 |
| $C_{5+}$ | 63 | 0 | 0 | 0 | 0 |
| $C_2H_4$ | 0 | 0 | 228 | 228 | 981 |
| $C_3H_6$ | 0 | 0 | 473 | 0 | 0 |
| $C_4H_8$ | 0 | 0 | 0 | 0 | 0 |

TABLE 3

Major Stream Information for the configuration in FIG. 3A wherein the two dehydrogenation reactors are at high pressures (9~10 bar)

|  | Sweet and dry shale gas 301A | Propane dehydrogenation inlet 302A | Propane dehydrogenation outlet 303A | Ethane dehydrogenation inlet 304A | Ethane dehydrogenation outlet 305A |
|---|---|---|---|---|---|
| Temperature (° C.) | 25 | 650 | 650 | 850 | 850 |
| Pressure (bar) | 30 | 9.58 | 9.37 | 9.16 | 8.95 |
| Flowrate (kmol/h) | 4749 | 5074 | 5637 | 5410 | 6300 |
| $N_2$ | 78 | 78 | 78 | 78 | 78 |
| $H_2$ | 0 | 0 | 473 | 473 | 1263 |
| $CH_4$ | 2866 | 2866 | 2956 | 2956 | 3156 |
| $C_2H_6$ | 991 | 991 | 990 | 1812 | 822 |
| $C_3H_8$ | 563 | 1140 | 577 | 0 | 0 |
| $C_4H_{10}$ | 188 | 0 | 0 | 0 | 0 |
| $C_{5+}$ | 63 | 0 | 0 | 0 | 0 |
| $C_2H_4$ | 0 | 0 | 90 | 90 | 981 |
| $C_3H_6$ | 0 | 0 | 473 | 0 | 0 |
| $C_4H_8$ | 0 | 0 | 0 | 0 | 0 |

TABLE 4

Major Stream Information for the configuration in FIG. 3B with two H2 separation units

| | Sweet and dry shale gas 301B | Propane dehydrogenation inlet 302B | Propane dehydrogenation outlet 303B | Ethane dehydrogenation inlet 304B | Ethane dehydrogenation outlet 305B |
|---|---|---|---|---|---|
| Temperature (° C.) | 25 | 650 | 650 | 850 | 850 |
| Pressure (bar) | 30 | 2.58 | 2.37 | 2.16 | 1.95 |
| Flowrate (kmol/h) | 4749 | 5275 | 6611 | 4242 | 5066 |
| $N_2$ | 78 | 78 | 78 | 78 | 78 |
| $H_2$ | 0 | 520 | 1060 | 0 | 723 |
| $CH_4$ | 2866 | 2866 | 2956 | 2956 | 3156 |
| $C_2H_6$ | 991 | 991 | 923 | 1051 | 127 |
| $C_3H_8$ | 563 | 872 | 309 | 0 | 0 |
| $C_4H_{10}$ | 188 | 0 | 0 | 0 | 0 |
| $C_{5+}$ | 63 | 0 | 0 | 0 | 0 |
| $C_2H_4$ | 0 | 0 | 157 | 157 | 980 |
| $C_3H_6$ | 0 | 0 | 473 | 0 | 0 |
| $C_4H_8$ | 0 | 0 | 0 | 0 | 0 |

TABLE 5

Major Stream Information for the configuration in FIG. 3B with only one H2 separation unit after C1/C2 separation

| | Sweet and dry shale gas 301B | Propane dehydrogenation inlet 302B | Propane dehydrogenation outlet 303B | Ethane dehydrogenation inlet 304B | Ethane dehydrogenation outlet 305B |
|---|---|---|---|---|---|
| Temperature (° C.) | 25 | 650 | 650 | 850 | 850 |
| Pressure (bar) | 30 | 2.58 | 2.37 | 2.16 | 1.95 |
| Flowrate (kmol/h) | 4749 | 5275 | 6611 | 5429 | 6253 |
| $N_2$ | 78 | 78 | 78 | 78 | 78 |
| $H_2$ | 0 | 520 | 1060 | 1060 | 1783.4 |
| $CH_4$ | 2866 | 2866 | 2956 | 2956 | 3156 |
| $C_2H_6$ | 991 | 991 | 923 | 1178 | 254 |
| $C_3H_8$ | 563 | 872 | 309 | 0 | 0 |
| $C_4H_{10}$ | 188 | 0 | 0 | 0 | 0 |
| $C_{5+}$ | 63 | 0 | 0 | 0 | 0 |
| $C_2H_4$ | 0 | 0 | 157 | 157 | 981 |
| $C_3H_6$ | 0 | 0 | 473 | 0 | 0 |
| $C_4H_8$ | 0 | 0 | 0 | 0 | 0 |

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges appear in one or more claims below. All numerical values are "about" or "approximately" the indicated value, meaning the values take into account experimental error, machine tolerances and other variations that would be expected by a person having ordinary skill in the art.

The foregoing has also outlined features of several embodiments so that those skilled in the art can better understand the present disclosure. Those skilled in the art should appreciate that they can readily use the present disclosure as a basis for designing or modifying other methods or devices for carrying out the same purposes and/or achieving the same advantages of the embodiments disclosed herein. Those skilled in the art should also realize that such equivalent constructions do not depart from the spirit and scope of the present disclosure, and that they can make various changes, substitutions, and alterations herein without departing from the spirit and scope of the present disclosure, and the scope thereof is determined by the claims that follow.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

What is claimed is:

1. A process for dehydrogenation of alkane or alkane mixtures, comprising:
   providing a hydrocarbon feed stream comprising methane, ethane, and propane;
   dehydrogenating the hydrocarbon feed stream in a first reactor at conditions sufficient to convert propane to propylene to provide a first dehydrogenation reactor effluent comprising propylene, methane, ethane, and unreacted propane;
   separating a stream comprising methane and ethane from the first dehydrogenation reactor effluent to provide a separated stream comprising methane and ethane; and
   dehydrogenating the separated stream comprising methane and ethane from the first dehydrogenation reactor effluent in a second reactor at conditions sufficient to convert ethane to ethylene to provide a second dehydrogenation reactor effluent comprising ethylene.

2. The process of claim 1, wherein the concentration of methane in the hydrocarbon feed stream is at least 30 mol % and the concentration of propane and ethane combined is at least 5 mol %, and propane concentration is at least 2 mol %.

3. The process of claim 1, wherein the hydrocarbon feed stream is a shale gas stream or a natural gas stream.

4. The process of claim 1, wherein propylene is recovered as product from the first dehydrogenation reactor effluent.

5. The process of claim 1, wherein the unreacted propane in the first dehydrogenation reactor effluent is separated and recycled to the first reactor.

6. The process of claim 5, wherein a portion of the separated propane is recovered as a product.

7. The process of claim 1, wherein ethylene is recovered as product from the second dehydrogenation reactor effluent.

8. The process of claim 1, wherein ethane is separated from the second dehydrogenation reactor effluent and recycled to the second dehydrogenation reactor.

9. The process of claim 1, wherein ethane is separated from the second dehydrogenation reactor effluent and recovered as a product.

10. The process of claim 1, wherein hydrogen is separated from the first dehydrogenation reactor effluent or the second dehydrogenation reactor effluent or both effluents, and a portion of the separated hydrogen is fed to the first reactor.

11. The process of claim 10, wherein a hydrogen to propane ratio is 0.1:1 to 1:1.

12. The process of claim 1, wherein at least one of the dehydrogenation reactors is an electrically heated reactor.

13. The process of claim 1, wherein at least one of the ethylene and propylene products is further oligomerized into one or more liquid hydrocarbons.

14. A process for dehydrogenation of alkane or alkane mixtures, comprising:
providing a hydrocarbon feed stream comprising methane, ethane, propane, and butane;
dehydrogenating the hydrocarbon feed stream in a first reactor at conditions sufficient to convert propane to propylene and to convert butane to butylene, providing a first dehydrogenation reactor effluent comprising propylene, butylene, methane, ethane, unreacted propane, and unreacted butane;
separating a stream comprising methane and ethane from the first dehydrogenation reactor effluent to provide a separated stream comprising methane and ethane; and
dehydrogenating the separated stream comprising methane and ethane from the first dehydrogenation reactor effluent in a second reactor at conditions sufficient to convert ethane to ethylene to provide a second dehydrogenation reactor effluent comprising ethylene.

15. The process of claim 14, wherein the concentration of methane in the hydrocarbon feed stream is at least 30 mol % and the concentration of ethane, propane and butane combine is at least 5 mol %, and the combined propane and butane concentration is at least 2 mol %.

16. The process of claim 14, wherein the hydrocarbon feed stream is a shale gas stream or a natural gas stream.

17. The process of claim 14, wherein the propylene and butylene are recovered as product from the first dehydrogenation reactor effluent.

18. The process of claim 14, wherein the unreacted propane and butane from the first dehydrogenation reactor effluent are separated and recycled to the first dehydrogenation reactor.

19. The process of claim 14, wherein the unreacted ethane from the second dehydrogenation reactor effluent is separated and recycled to the second dehydrogenation reactor.

20. The process of claim 14, wherein a portion of the propane or butane is recovered as a product.

21. The process of claim 14, wherein a portion of the ethane is recovered as a product.

22. The process of claim 14, wherein hydrogen is separated from the first dehydrogenation reactor effluent or the second dehydrogenation reactor effluent or both effluents, and a portion of the separated hydrogen is fed to the first reactor.

23. The process of claim 14, wherein a hydrogen to propane ratio is 0.1:1 to 1:1.

24. The process of claim 14, wherein at least one of the dehydrogenation reactors is an electrically heated reactor.

25. The process of claim 14, wherein at least one of the ethylene, propylene and butylene products is further oligomerized into one or more liquid hydrocarbons.

* * * * *